United States Patent
Estwanik

[11] Patent Number: 6,013,044
[45] Date of Patent: *Jan. 11, 2000

[54] HAND AND WRIST STABILIZATION DEVICE

[76] Inventor: Joseph J. Estwanik, 335 Billingsley Rd., Charlotte, N.C. 28211

[*] Notice: Under 35 U.S.C. 154(b), the term of this patent shall be extended for 667 days.

[21] Appl. No.: 08/498,884

[22] Filed: Jul. 6, 1995

Related U.S. Application Data

[63] Continuation of application No. 29/023,620, May 27, 1994, Pat. No. Des. 367,731.

[51] Int. Cl.⁷ .............................. A61F 13/00; A41D 13/10
[52] U.S. Cl. ................................ 602/64; 602/21; 602/61; 2/18; 2/161.1; 2/161.4
[58] Field of Search .................... 2/16, 18, 20, 161.1, 2/161.3, 161.4; 128/878, 879, 880; 602/20, 21, 60, 61, 62, 64; 482/44, 46, 48, 55

[56] References Cited

U.S. PATENT DOCUMENTS

| | | |
|---|---|---|
| 1,627,382 | 5/1927 | Golomb ........................................ 2/18 |
| 1,706,503 | 3/1929 | Travers ........................................ 2/18 |
| 4,287,609 | 9/1981 | Amadeo . |
| 5,014,689 | 5/1991 | Meunchen et al. . |
| 5,018,221 | 5/1991 | Romandetto . |
| 5,295,269 | 3/1994 | Ballard . |

Primary Examiner—Richard J. Apley
Assistant Examiner—Kim M. Lee
Attorney, Agent, or Firm—Kennedy Covington Lobdell & Hickman LLP

[57] ABSTRACT

A hand and wrist stabilization device for disposition on the hand and wrist of a user internally of a boxing glove to reduce relative movement of internal hand elements, specifically, the metacarpophalangeal joints, during impact resulting from boxing activities includes a flexible body, a metacarpophalangeal joint force dispersion pad attached to the body, an ulnar wrist stabilization strap, a radial wrist stabilization strap, and a contoured wrist compression strap attached to the body portion and a metacarpophalangeal joint stabilization member attached to the body all act to disperse force on the metacarpophalangeal joints while stabilizing the metacarpophalangeal joints against internal movement caused by impact force transmitted thereto during boxing activities.

14 Claims, 7 Drawing Sheets

HAND AND WRIST STABILIZATION DEVICE

CROSS-REFERENCE TO RELATED APPLICATION

The present application is a continuation of U.S. Design patent application Ser. No. 29/023,620 filed May 27, 1994 now U.S. Pat. No. Des. 367,731, for HAND WRAP FOR USE IN CONTACT RELATED ACTIVITIES.

BACKGROUND OF THE INVENTION

The present invention relates broadly to muscle and joint braces and, more particularly, to a device for stabilizing the hand and wrist of a user while the hand is clenched into a fist for use during boxing activities.

When considering boxing injuries, most people think of injuries related to getting batted freely about the head and torso. Nevertheless, even though the hand is covered by the boxing glove, the hand and, more particularly, the metacarpophalangeal (MCP) joints are subject to injury due primarily to displacement or derangement caused by repeated trauma. Hand injury and reinjury in boxing can be lessened by increasing the application of various safety measures including methods of wrapping and gloving the hands and usage of custom-fit protective devices.

Typically, pads are placed over the knuckles of a boxer and taped into place which, if skillfully done, can strengthen the wrist and hand. However, care must be used when applying the tape which can be a time-consuming process.

Therefore, if the boxer desires hand stabilization and accompanying knuckle or MCP joint protection, a lengthy, dependent on the skill and knowledge of the applier, and time-consuming wrapping and taping process must be undertaken in order to properly stabilize the boxer's hand.

SUMMARY OF THE INVENTION

It is accordingly an object of the present invention to provide a hand and wrist stabilization device which is adaptable for most any boxer and provides swift and sure hand and wrist stabilization.

It is another object of the present invention to provide such a device which is essentially a one-piece unit in that all attached members are attached to a central hand covering.

It is another object of the present invention to provide such a hand and wrist stabilization device that provides enhanced MCP joint stabilization over the current state of the art.

To that end, a hand and wrist stabilization device for disposition on the hand and wrist of a user inside a boxing glove is provided to reduce relative movement of internal hand elements during impact resulting from competitive boxing, aerobic boxing martial arts, law enforcement training or other activities that involve striking or punching, that includes a body formed of flexible material for disposition over the hand and the wrist of a user, the body including a hand portion and a wrist portion; a metacarpophalangeal (MCP) joint force dispersion pad mounted to the body portion and extending transversely across at least a portion of the MCP joints of a hand on which the device is worn for dispersal of an impact force to reduce the force transmitted to the metacarpophalangeal joints. The device further includes a strap, i.e., a radial wrist stabilization strap, that extends laterally away from the pad and an arrangement for fastening the strap to the body at the wrist portion when the hand is formed, or clenched, into a fist for limiting wrist movement during hand movement.

It is preferred that the present invention include a second strap, i.e., an ulnar wrist stabilization strap, that extends laterally away from the body portion oppositely from the first strap and fastenable to the wrist portion oppositely from the first strap. Preferably, the present invention includes a wrist compression strap attached to the body portion and configured to extend in a circumferential disposition around the wrist portion and an arrangement for releasably retaining the wrist compression strap in the circumferential disposition to enhance the ability of the wrist to resist lateral flexion or extension movement and to assist the strap fastening arrangement in retaining all three straps against the wrist portion.

It is preferred that the present invention include a metacarpophalangeal joint stabilization member mounted to the hand portion at a position oppositely disposed from the force dispersion pad with the user's hand disposed therebetween for enhanced stabilization of the user's MCP joints. Preferably, the stabilization member is disposed adjacent an underside of the MCP joints of a user.

It is preferred that the first strap, i.e., the radial wrist stabilization strap extend away from the dispersion pad for attachment to the wrist portion when the user's hand is formed into a fist to resist radial movement of the wrist during boxing, striking or punching activities. It is further preferred that the second strap, i.e., the ulnar wrist stabilization strap, extend away from the force dispersion pad for attachment to the wrist portion when the user's hand is formed into a fist to resist ulnar movement of the wrist during striking or punching activities.

By the above, the present invention provides a simple, easy to use hand and wrist stabilization device which may be rapidly attached to a boxer's hand to provide enhanced hand and wrist stabilization and support during boxing, martial arts or other activities involving striking or punching.

DETAILED DESCRIPTION OF THE PREFERRED EMBODIMENT

Figure 1:
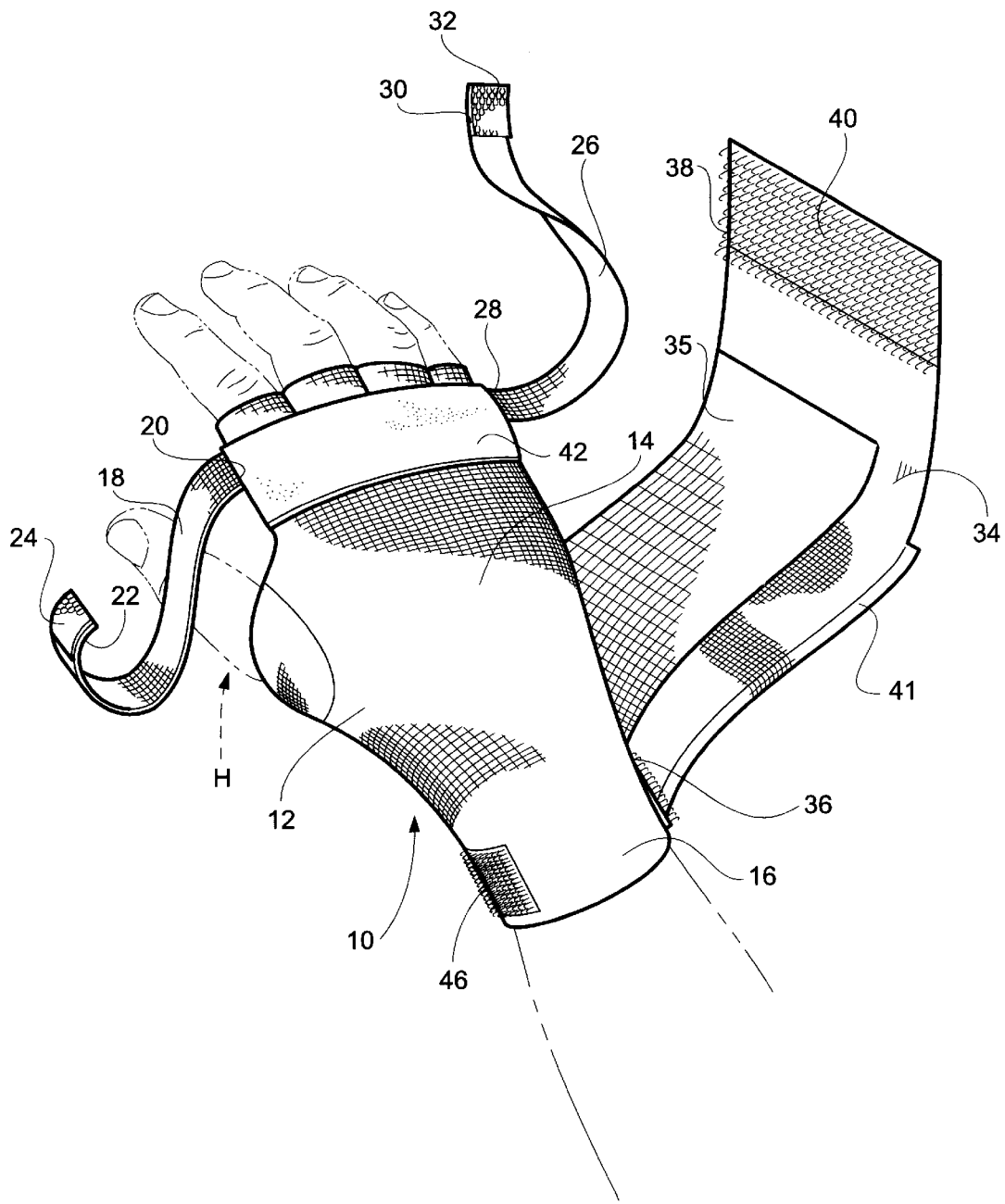
FIG. 1 is a top perspective view of a hand and wrist stabilization device according to the preferred embodiment of the present invention.
Figure 2:
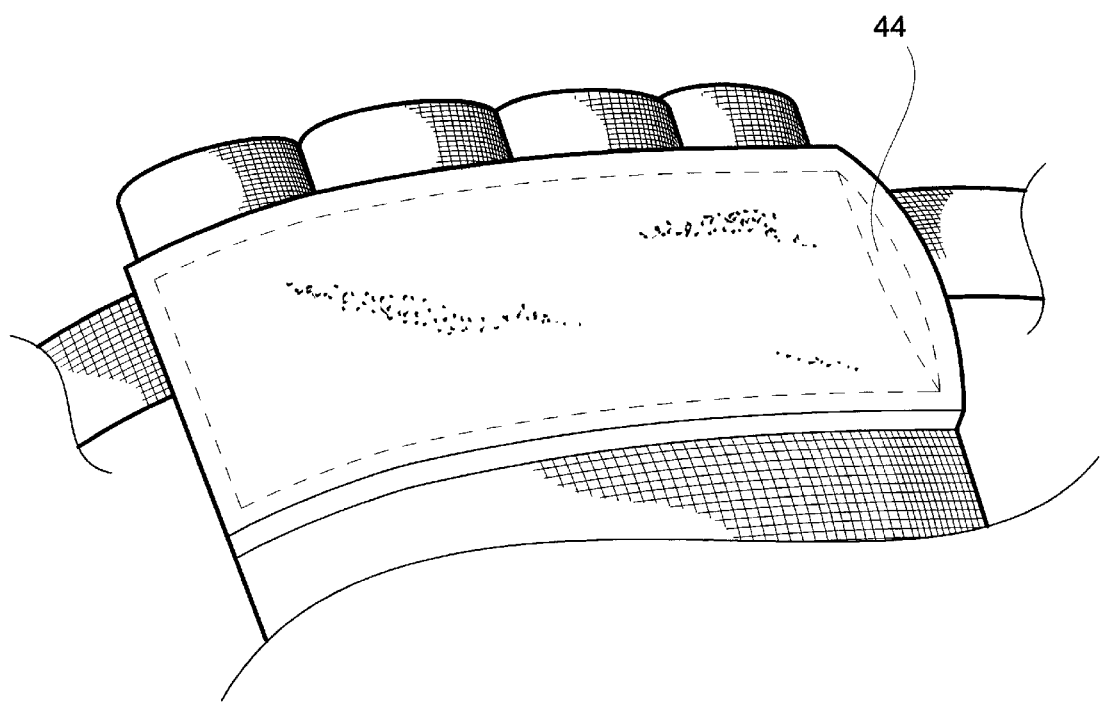
FIG. 2 is a perspective view of the optional dispersion pad receiving pocket associated with the hand and wrist stabilization device according to a second preferred embodiment thereof.

Turning now to the drawings and, more particularly to FIG. 1, a hand and wrist stabilization device is illustrated generally at 10 and includes a body 12 for substantially enveloping the hand and wrist of a user. The body 12 includes a hand portion 14 which covers the major portions of a user's hand while leaving the fingers and thumb exposed, and a wrist portion 16 which extends along the user's arm slightly beyond the wrist area the body 12 may be formed of any suitable flexible material, including textile material, vinyl or leather. A generally rectangular force dispersion pad is mounted to the hand portion 14 and extends across the metacarpophalangeal (MCP) joints of the user's hand. As seen in FIG. 2, a receiving pocket 44 may be disposed in place of the force dispersion pad 42 so that interchangeable force dispersion pads of various thicknesses may be inserted into the receiving pocket 44. It is also contemplated that the pocket 44 be sewn closed to contain a single, non-interchangeable force dispersion pad 42. A radial wrist stabilization strap 18 is formed as a flexible elongate member and extends outwardly from a mounted strap portion 20 which is attached to the hand portion 14 to a distal strap portion 22. The radial wrist stabilization strap 18 formed of flexible material and is disposed on the thumb side of the user's hand.

An ulnar wrist stabilization strap 26 extends outwardly from a mounted strap portion 28 attached to the hand portion 14 to a distal strap portion 30 at a position oppositely from the radial wrist stabilization strap 18. The ulnar wrist stabilization strap 26 is also formed of flexible material.

Figure 7:
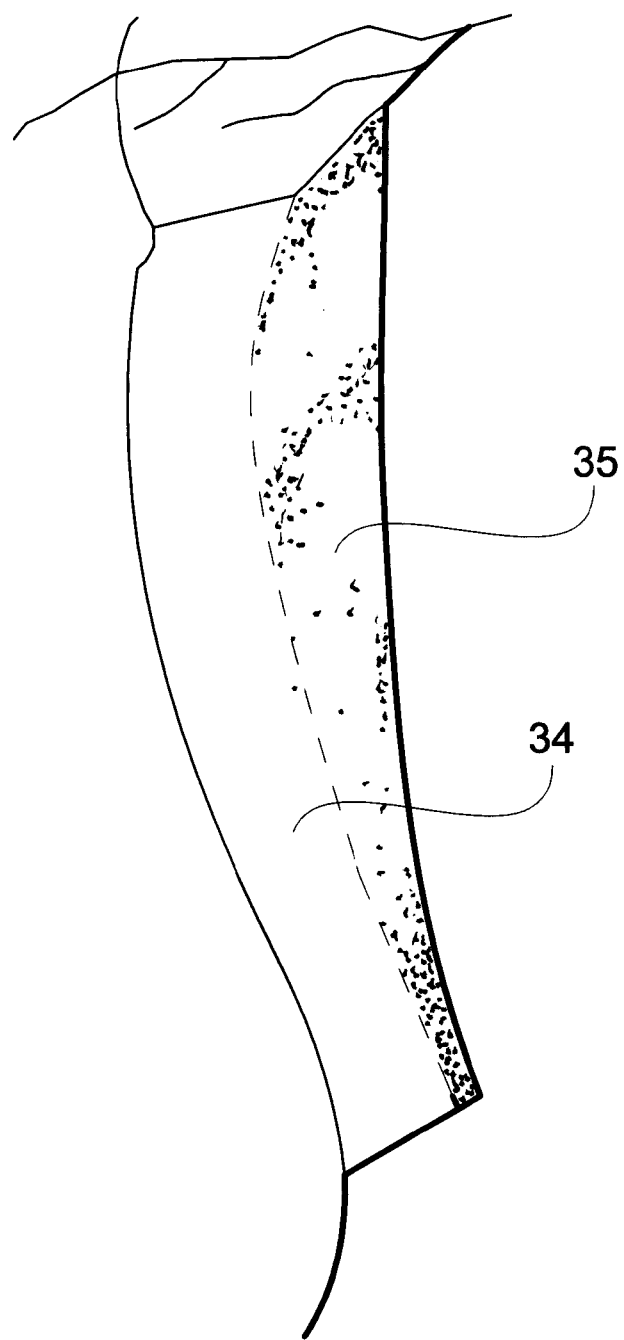
FIG. 7 is a cutaway view of a portion of the wrist compression strap taken along line 7—7 of FIG. 6.

A contoured wrist compression strap is attached to the wrist portion 16 to extend outwardly therefrom and is attached to the wrist portion 16 at one end 36 thereof. The contoured wrist compression strap 34 includes extra contoured padding 35 which substantially conforms to the shape of the wrist and hand as seen in FIG. 7. The contoured wrist compression strap 34 is thicker at the radial side of the wrist for added support.

Figure 6:
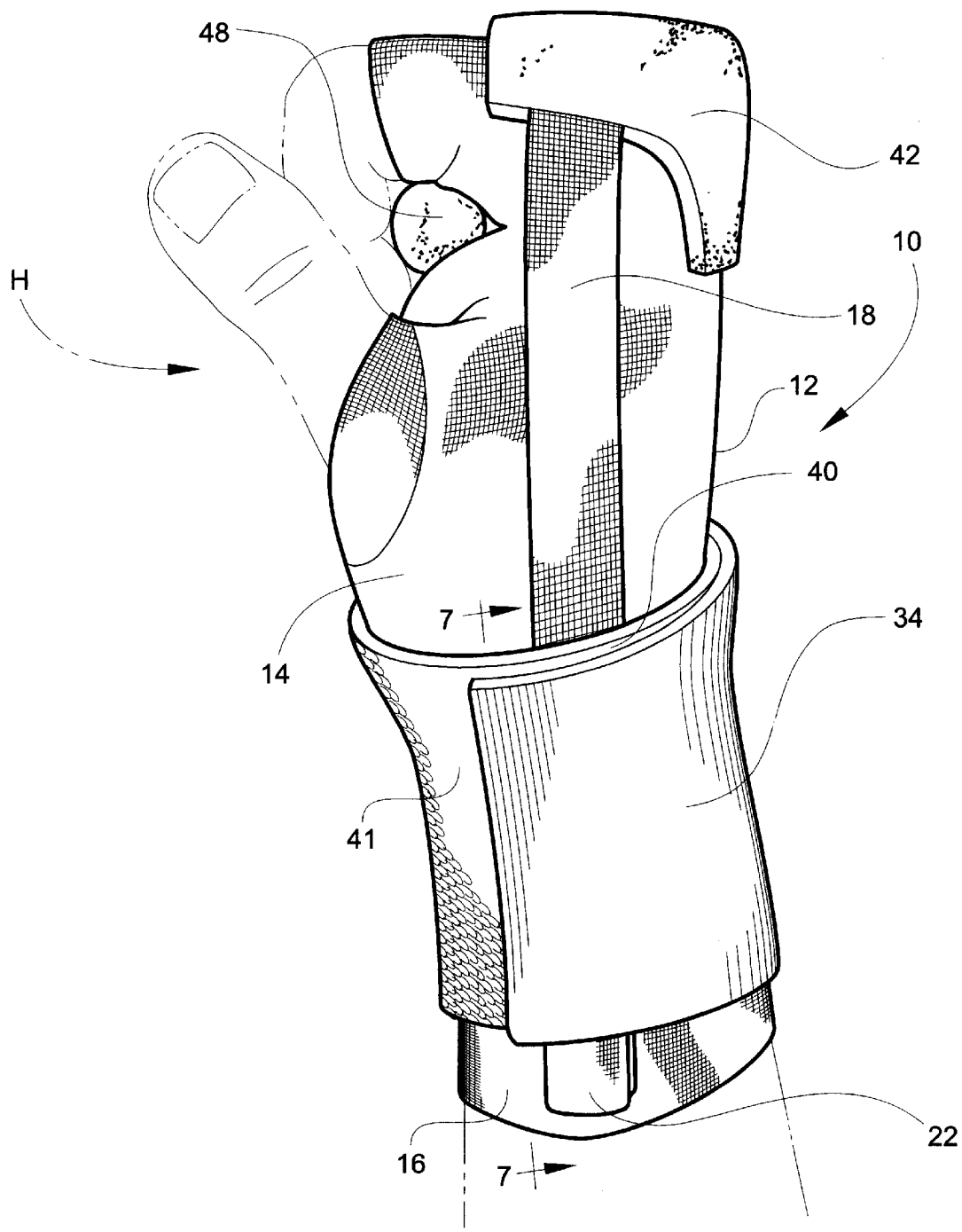
FIG. 6 is a left side view of the hand and wrist stabilization device illustrated in FIG. 4.

All three straps may be fastened to the wrist portion 16 preferably by using hook-and-loop type fasteners. To that end, one portion 46 of a hook-and-loop fastener is attached to the wrist portion 46 adjacent the end thereof. The one portion 46 may extend around the wrist portion or may exist as two separate members, one disposed on either side of the wrist portion 16. A second portion of the hook-and-loop fastener is attached to the distal end 22 of the radial wrist stabilization strap 18, and a second hook-and-loop fastener portion 32 is attached to the distal end portion 30 of the ulnar wrist stabilization strap 26 and positioned for attachment to the first portion of the hook-and-loop type fastener 46, as will be seen in greater detail hereinafter The wrist compression strap 34 is longer than the circumference of the wrist portion 14 and thereby wraps around the wrist portion to overlap itself, as seen in FIG. 6. For securement, a first hook-and-loop fastener portion 40 is attached to the distal end portion 38 of the contoured wrist compression strap 34. A second hook-and-loop fastener portion 41 is attached to the outer surface of the wrist portion 16 and is positioned for mating engagement with the first hook-and-loop fastener portion 40. As will be appreciated by those skilled in the art, the hook-and-loop type fastener is preferred for its ease of use but other types of fasteners, such as snaps, may be used without departing from the spirit and scope of the present invention.

Figure 3:
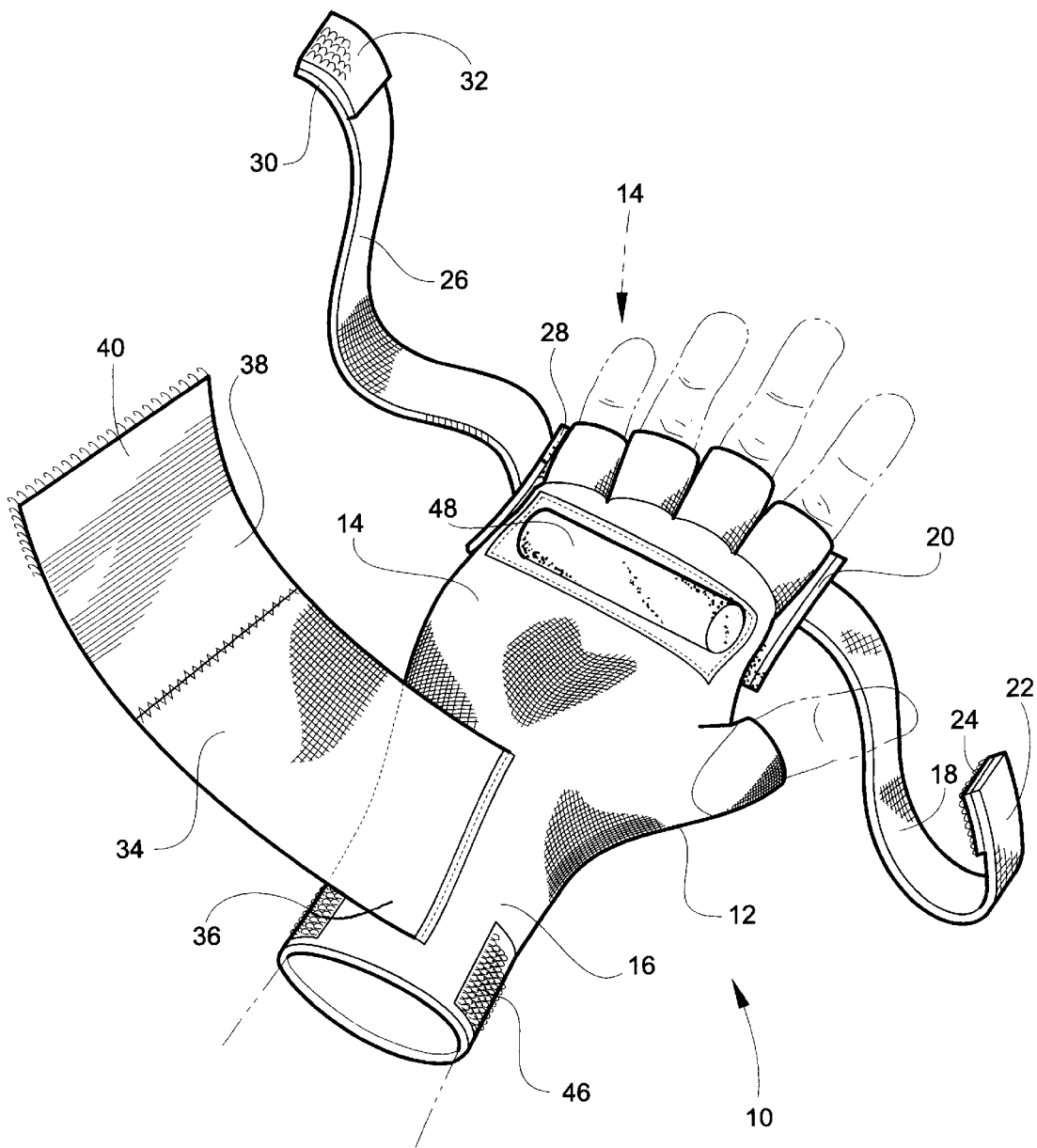
FIG. 3 is a bottom perspective view of the hand and wrist stabilization device illustrated in FIG. 1.

With reference to FIG. 3, a metacarpophalangeal joint stabilization member 48 is formed as a cylindrical, padded member and is disposed on the inner side of the hand portion 14 to extend transversely along the underside of the metacarpophalangeal joints of the hand H of the user. Although not depicted herein, it should be understood that the metacarpophalangeal joint stabilization member 48 may be molded or otherwise formed with a hand contour. As can also be seen in FIG. 3, the preferred mounting location of the contoured wrist compression strap 34 is with its mounted end 36 along the inner portion of the wrist portion 16, relative to the user's hand H.

Figure 4:
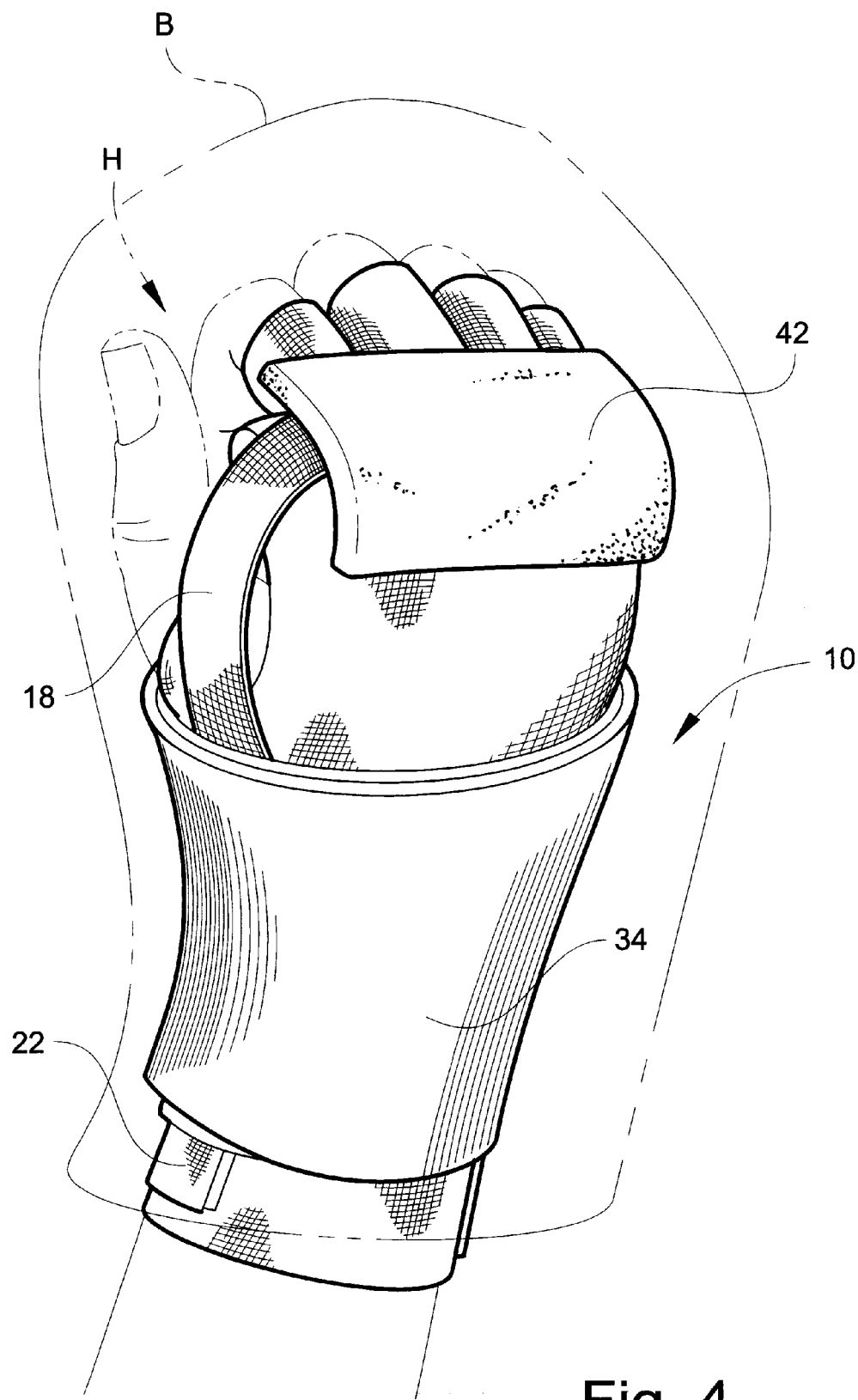
FIG. 4 is a perspective view of the hand and wrist stabilization device illustrated in FIG. 1 in operation.
Figure 5:
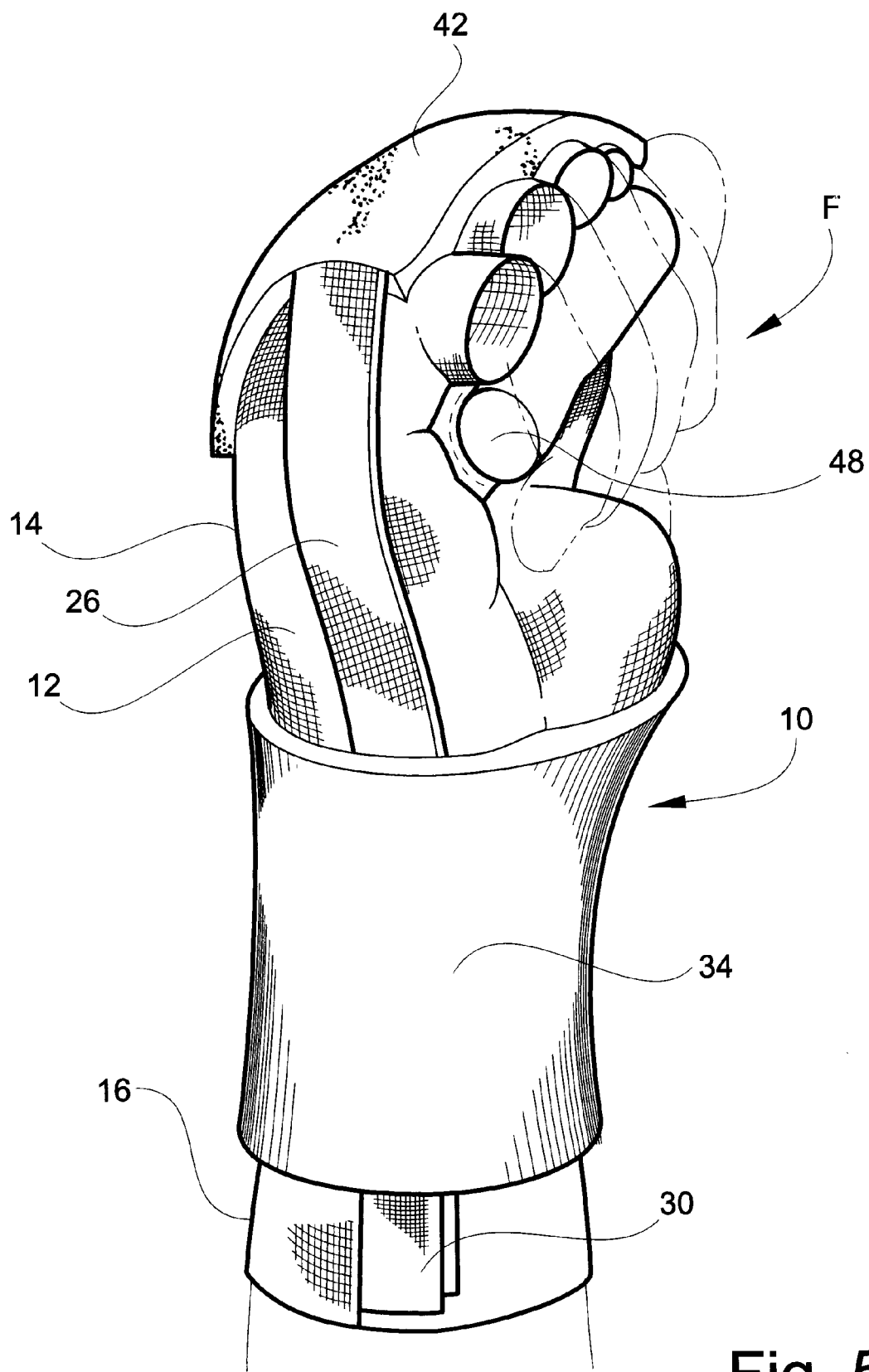
FIG. 5 is a right side view of the hand and wrist stabilization device illustrated in FIG. 4.

Operation of the device is best seen in FIGS. 4–6. In FIG. 4, the device 10 is illustrated on the hand H of a user disposed internally of a boxing glove illustrated in phantom at B. To use the device, the user's hand H is positioned within the body portion 12 with the fingers and thumbs extending through openings provided therefor and the device 10 surrounding the user's hand and wrist, as illustrated in FIGS. 1 and 3. The hand is then clenched into a fist as if gripping the metacarpophalangeal joint stabilization member 48, as illustrated in FIG. 4. The radial wrist strap 18 and the ulnar wrist strap 26 secured to either side of the wrist portion 16 at the respective fastener portions 46. The contoured wrist compression strap 34 is then wrapped around the hand to overlap a portion of itself and secured onto hook-and-loop material 41 attached to itself.

As seen in FIG. 5, the user's fingers F are wrapped around the metacarpophalangeal joint stabilization member 48 and the combination of this stabilization member 48 with the wrist stabilization straps 18,26,34 acts to prevent relative movement of the internal hand elements under forces due to impact, particularly the metacarpophalangeal joints. As seen in FIG. 6, the force dispersion pad 42 acts in concert with the stabilization straps 18,26,34 to protect the hand by reducing the force at each metacarpophalangeal joint.

As can be seen from the above, the combination of the force dispersion pad which relieves the impact force on the metacarpophalangeal joints, and the stabilization member in combination with the stabilization straps reduces internal movement of the metacarpophalangeal joints which can substantially reduce hand injury for those engaged in boxing activities.

By the above, the present invention provides an easy-to-use and effective method for protecting the hands during boxing activities.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A hand and wrist stabilization device for disposition on the hand and wrist of a user internally of a boxing glove to reduce relative movement of internal hand elements during impact resulting from boxing activities, said device comprising:

a body formed of flexible material for disposition over at least a portion of the hand and wrist, said body including a hand portion and a wrist portion;

a force dispersion pad mounted to said body portion and extending transversely across at least a portion of the metacarpophalangeal joints of a hand on which the device is worn for dispersal of an impact force to reduce the force transmitted to the metacarpophalangeal joints;

a strap extending laterally away from said pad from a position adjacent the metacarpophalangeal joints;

means for fastening said strap to said body at said wrist portion when the hand is formed into a fist for isolating wrist movement during hand movement; and a metacarpophalangeal joint stabilization member mounted to said hand portion at a position oppositely disposed from said force dispersion pad with the user's hand disposed therebetween for enhanced stabilization of the user's metacarpophalangeal joints.

2. A hand and wrist stabilization device according to claim 1 and further comprising a second strap extending laterally away from said body portion oppositely from said first strap and fastenable to said wrist portion oppositely from said first strap.

3. A hand and wrist stabilization device according to claim 2 wherein said second strap forms an ulnar wrist stabilization strap extending away from said dispersion pad for attachment to said wrist portion when the user's hand is clenched into a fist.

4. A hand and wrist stabilization device according to claim 1 and further comprising a wrist compression strap attached to said body portion and configured to extend in a circumferential disposition around said wrist portion and means for releasably retaining said wrist compression strap in said circumferential disposition to enhance the ability of the wrist to resist lateral movement and to assist said strap fastening means in retaining said straps against said wrist portion.

5. A hand and wrist stabilization device according to claim 4 wherein said wrist compression strap is formed to generally conform to wrist and hand shape and includes padding material disposed at a position corresponding to the radial side of the user's wrist.

6. A hand and wrist stabilization device according to claim 1 wherein said stabilization member mounted to said body portion corresponding to the underside of the metacarpophalangeal joints of a user.

7. A hand and wrist stabilization device according to claim 1 wherein said first strap forms a radial wrist stabilization strap extending away from said dispersion pad for attachment to said wrist portion when the user's hand is clenched into a fist to resist radial movement of the wrist during boxing activities.

8. A hand and wrist stabilization device for disposition on the hand and wrist of a user internally of a boxing glove to reduce relative movement of internal hand elements during impact resulting from boxing activities, said device comprising:

a body formed of flexible material for disposition over at least a portion of the hand and wrist, said body including a hand portion and a wrist portion;

a force dispersion pad mounted to said body portion and extending transversely across at least a portion of the metacarpophalangeal joints of a hand on which the device is worn for dispersal of an impact force to reduce the force transmitted to the metacarpophalangeal joints;

a strap extending laterally away from said pad from a position adjacent the metacarpophalangeal joints; and means for fastening said strap to said body at said wrist portion when the hand is formed into a fist for isolating wrist movement during hand movement;

wherein said hand portion includes a receiving pocket and said dispersion pad is removably disposed therein wherein said dispersion pad may be interchanged with other dispersion pads.

9. A hand and wrist stabilization device for disposition on the hand and wrist of a user internally of a boxing glove to reduce relative movement of internal hand elements during impact resulting from boxing activities, said device comprising:

a body formed of flexible material for disposition over the hand and wrist of a user, leaving the fingers and thumb exposed, said body including a hand portion and a wrist portion;

a metacarpophalangeal joint force dispersal pad mounted to said body portion and extending transversely across at least a portion of the metacarpophalangeal joints of a user's hand for dispersal of an impact force to reduce the force transmitted to the metacarpophalangeal joints;

a pair of straps extending away from said dispersion pad at a position adjacent the metacarpophalangeal joints for attachment to said wrist portion when said user's hand is formed into a fist; and a metacarpophalangeal joint stabilization member mounted to said hand portion oppositely disposed from said force dispersion pad with the user's hand disposed therebetween for stabilization of the user's metacarpophalangeal joints during boxing activities.

10. A hand and wrist stabilization device according to claim 9 and further comprising a metacarpophalangeal joint stabilization member mounted to said hand portion at a position oppositely disposed from said force dispersion pad with the user's hand disposed therebetween for stabilization of the user's metacarpophalangeal joints.

11. A hand and wrist stabilization device according to claim 9 and further comprising a wrist compression strap attached to said body portion and configured to extend in a circumferential disposition around said wrist portion and means for releasably retaining said wrist compression strap in said circumferential disposition to enhance the ability of the wrist to resist lateral movement and to assist said strap fastening means in retaining said straps against said wrist portion.

12. A hand and wrist stabilization device according to claim 11 wherein said wrist compression strap is contoured to generally conform to wrist and hand shape and is thickened by the addition of padding material at the radial side of the user's wrist.

13. A hand and wrist stabilization device according to claim 9 wherein said stabilization member is disposed adjacent an underside of the metacarpophalangeal joints of a user.

14. A hand and wrist stabilization device according to claim 9 wherein said second strap forms an ulnar wrist stabilization strap extending away from said dispersion pad for attachment to said wrist portion when said user's hand is formed into a fist.

* * * * *